United States Patent
Albanna et al.

(10) Patent No.: US 12,134,792 B1
(45) Date of Patent: Nov. 5, 2024

(54) PROCESS FOR PRODUCTION OF A SOLUBLE AND INSOLUBLE COLLAGEN PRODUCT FROM MAMMALIAN DERMIS TISSUE

(71) Applicant: Humabiologics, Inc., Phoenix, AZ (US)

(72) Inventors: Mohammad Z. Albanna, Chandler, AZ (US); Nilabh S. Kajave, Tempe, AZ (US)

(73) Assignee: Humabiologics, Inc., Phoenix, AZ (US)

( * ) Notice: Subject to any disclaimer, the term of this patent is extended or adjusted under 35 U.S.C. 154(b) by 0 days.

(21) Appl. No.: 18/654,723

(22) Filed: May 3, 2024

Related U.S. Application Data

(60) Provisional application No. 63/463,579, filed on May 3, 2023.

(51) Int. Cl.
| | | |
|---|---|---|
| *C12P 21/06* | (2006.01) | |
| *A23J 1/10* | (2006.01) | |
| *A61K 38/17* | (2006.01) | |
| *C07K 1/14* | (2006.01) | |
| *C07K 14/78* | (2006.01) | |
| *C12P 21/02* | (2006.01) | |

(52) U.S. Cl.
CPC .................................. *C12P 21/02* (2013.01)

(58) Field of Classification Search
CPC . C12P 21/06; C07K 1/14; C07K 14/78; A23J 1/10; A61K 38/17
See application file for complete search history.

(56) References Cited

U.S. PATENT DOCUMENTS

| | | |
|---|---|---|
| 4,784,986 A | 11/1988 | Usher |
| 4,969,912 A | 11/1990 | Kelman et al. |
| 5,677,284 A | 10/1997 | Li |
| 5,980,946 A | 11/1999 | Jones et al. |
| 6,548,189 B1 | 4/2003 | Gunasekaran |
| 6,936,271 B1 | 8/2005 | Oliver et al. |
| 10,709,810 B2 | 7/2020 | Sun et al. |
| 10,821,205 B2 | 11/2020 | Xu et al. |
| 2007/0014773 A1 | 1/2007 | Matheny et al. |
| 2015/0313623 A1 | 11/2015 | Bellomo et al. |
| 2019/0247287 A1 | 8/2019 | Pinsky |
| 2019/0351097 A1 | 11/2019 | Voytik-Harbin |
| 2020/0093799 A1 | 3/2020 | Dreher |

OTHER PUBLICATIONS

Matinong et al., Biology 2022, 11, 905. https://doi.org/10.3390/biology11060905.*

* cited by examiner

*Primary Examiner* — Maryam Monshipouri
(74) *Attorney, Agent, or Firm* — Invention To Patent Services; Alex Hobson

(57) ABSTRACT

A process for the production of a soluble collagen product and an insoluble collagen product from mammalian dermis tissue is described. The tissue may initially be processed to remove the epidermis and adipose tissue and then minced into small pieces. The process includes washing the minced dermis in an enzymatic solution, such as an amylase solution followed by homogenizing the amylased tissue. The soluble and insoluble collagen is then extracted from the homogenized tissue and subsequently separated into distinct soluble and insoluble fractions. The process produces collagen with high Dalton values that can subsequently be combined to produce a mixed composite collagen product. Also, the extracted collagen may be used as an integral composite collagen before separation.

14 Claims, 2 Drawing Sheets

PROCESS FOR PRODUCTION OF A SOLUBLE AND INSOLUBLE COLLAGEN PRODUCT FROM MAMMALIAN DERMIS TISSUE

CROSS REFERENCE TO RELATED APPLICATIONS

The application claims the benefit of priority to U.S. provisional patent application No. 63/463,579, filed on May 3, 2023; the entirety of which is hereby incorporated by reference herein.

BACKGROUND OF THE INVENTION

Field of the Invention

The invention relates to a process for the production of a soluble collagen product and an insoluble collagen product from mammalian dermis tissue.

Background

Collagen type I, the most prevalent protein in the human body, possesses a distinct triple helix structure that is composed of two pro-alpha ($\alpha_1$) polypeptide chains and one pro-alpha ($\alpha_2$) chain. This structure is built upon a repeating glycine-X-Y triplet, where X and Y commonly refer to proline and hydroxyproline amino acids. This unique arrangement provides collagen with exceptional biocompatibility, biodegradability, permeability, and fibrillogenesis. Collagen's ubiquitous nature, biological characteristics and ease of processing have allowed for its use in a range of different biomaterials-based applications including grafts and various manufactured products. However, collagen's weak mechanical properties and increased susceptibility to enzymatic degradation remain significant challenges.

SUMMARY OF THE INVENTION

The invention is directed to a process for the production of a soluble collagen product and an insoluble collagen product from mammalian dermis tissue. The process may utilize dermis tissue from any suitable mammal and in particular may use human dermis. The dermis may have adipose tissue as well as epidermis. The tissue may initially be processed to remove the epidermis and adipose tissue using conventional methods. The dermis tissue is preferably minced into small pieces have a maximum size, such as maximum length or width across the plane of the dermis, of no more than about 10 mm, no more than about 5 mm, no more than about 2 mm and any range between and including the minced dermis sizes provided. Smaller minced dermis may be preferred as it may enable faster processing due to the higher surface area of contact with the solutions. The process includes washing the minced dermis in an enzymatic solution, such as an amylase solution followed by homogenizing the amylased tissue. The soluble and insoluble collagen is then extracted from the homogenized tissue and subsequently separated into distinct soluble and insoluble fractions. The process produces collagen with high molecular weights expressed in Dalton values that can subsequently be combined to produce a mixed composite collagen product. Also, the extracted collagen may be used as an integral composite collagen before separation.

The minced dermis tissue may be washed in a lipid removal solution that is an amylase solution comprising an effective amount of amylase to remove the lipids and soften the tissue for extraction. The amylase solution may have a concentration of amylase from 0.01 mg/ml or more, 0.05 mg/ml or more, 0.1 mg/ml or more, 0.5 mg/ml or more, 1 mg/ml or more, 2 mg/ml or more and any other range between and including the amylase concentration. The amylase may be in a solution with water and may include a buffer, such as a phosphate buffer comprising phosphate. The concentration of phosphate may have a concentration of about 0.001 M or more, 0.01 M or more, 0.1M or more and any other range between and including the phosphate buffer concentration.

An exemplary lipid removal process includes washing the minced dermis tissue in a series of solutions, including a lipid removal solution and an organic solvent solution, such as an ethanol or other alcohol solution. A lipid removal solution may include chloroform, methanol and/or hexane. Other lipid removal solution or facilitator may be used in the lipid removal process including, but not limited to, a buffer solution used to maintain pH such as Phosphate Buffered Saline (PBS) or Tri Base, a surfactant, such as Triton, Ethylenediaminetetraacetic Acid (EDTA). A lipid removal solution may include a buffer and may also include an antifoaming agent such as Tributyl phosphate.

The minced dermis tissue may be washed in the lipid removal solution for a wash time of about 8 hours or more, about 10 hours or more about 20 hours or more, about 25 hours or more, about 30 hours or more and any range between and including the wash times.

The lipid removal solution may be cooled during the washing of the minced dermis tissue in the lipid removal solution. The lipid removal solution may be cooled to about 10° C. or less, about 8° C. or less, about 5° C. or less, and any range between and including the temperature values provided.

An exemplary ethanol solution includes ethanol with at least water, wherein the ethanol has a concentration of about 50% or more, about 60% or more, about 70% or more, about 80% or more and any range between and including the values provided, such as from about 60% to 70%, for example.

The minced dermis tissue may be washed in the ethanol solution for a wash time of about 1 hour or more, about 4 hours or more about 10 hours or more, about 16 hours or more, about 24 hours or from about 1 to 30 hours and any range between and including the wash times provided.

The ethanol solution may be cooled during the washing of the minced dermis tissue in the ethanol solution. The ethanol solution may be cooled to about 10° C. or less, about 8° C. or less, about 5° C. or less, and any range between and including the temperature values provided.

The process may wash the minced dermis in each of the organic and inorganic solvents one time each, two times each, three times each and even four times each or more.

The lipid removed dermis tissue is then homogenized while being maintained at a cold temperature to prevent degradation of the collagen, such as no more than 40° C. to produce homogenized tissue. It may be preferred to homogenize the lipid removed dermis tissue at a temperature near but above freezing, such as above freezing but below about 10° C., or below about 8° C., or below about 5° C. Homogenizing may be accomplished by blending, shearing or cutting the lipid-removed tissue.

The lipid-removed tissue is then subject to an extraction solution that utilizes an enzyme to extract the collagen by cleaving the telo regions of the collagen to release the collagen into solution. An exemplary pepsin solution may include an acid solution, such as an acetic acid solution combined with pepsin. The acid solution may have a molar concentration of about 0.1 M or more, about 0.5 M or more, about 1.0 M solution or more, about 2 M solution, about 2.5 M solution and any range between and including the molar concentrations provided. The pepsin may include the pepsin solution in a concentration of about 0.25 mg/ml or more, about 0.5 mg/ml or more about 0.75 mg/ml or more and 1.5 M solution or more, about 2 M solution, about 2.5 M solution and any range between and including the concentrations provided.

The lipid-removed tissue may be washed in the extraction solution for an extraction time of about 8 hours or more, about 24 hours or more about 48 hours or more, about 72 hours or more, about 96 hours or more and any range between and including the extraction times.

An exemplary extraction solution may be maintained in a temperature range of about 10° C. or less, about 8° C. or less, about 5° C. or less, and any range between and including the temperature values provided.

The extraction solution is typically agitated during collagen extraction to promote the solubilization of collagen from the extracellular matrix of the tissue source. Agitation helps to break down the tissue and expose the collagen fibers to the extraction solution, which contains acidic solutions to help denature the collagen and extract it from the tissue.

Agitation can help to improve the homogeneity of the collagen solution and reduce the formation of aggregates or clumps of collagen fibers.

Agitation can be achieved using various methods, such as mechanical stirring, shaking, or sonication. The level of agitation can affect the efficiency of collagen extraction, as higher levels of agitation can help to break down the tissue more quickly and increase the contact between the collagen fibers and the extraction solution.

Strong alkaline solution, such as sodium hydroxide solution can help to remove residual lipids, proteins, and other impurities from the tissue surface. This can help to improve the purity and yield of the extracted biomaterial. In addition, alkaline solution can also help to solubilize or denature certain types of extracellular matrix proteins, such as elastin or glycosaminoglycans, which may interfere with the extraction of the desired biomaterial, such as collagen. Alkaline solution treatment can also help to expose or unmask the collagen fibers in the tissue, making them more accessible to subsequent extraction steps. This can improve the efficiency of collagen extraction and help to minimize the use of harsher extraction methods that may damage the collagen fibers or alter their properties.

The soluble and insoluble collagen may then be separated through any conventional means including, but not limited to filtration, centrifugation, and the like.

A soluble collagen product, as defined herein will dissolve in an acid of Molar concentration of about 1 mM or more, about 5 mM or more, about 10 mM solution or more, about 50 mM solution, about 100 mM solution and any range between and including the molar concentrations provided.

An exemplary pH of the solution may be about 0.5 or more, about 1.0 or more, about 1.5 or more, about 2.0 or more, about 3.0 or more, about 4.0 or more and any range between and including the pH values provided.

The soluble collagen may be non-dialyzed collagen, or may be dialyzed to change molecular weight, remove impurities and/or adjust the pH.

The soluble collagen may further be lyophilized, including freezing the collagen and then heating the frozen collagen to a lyophilization temperature of at least 50° C. (70° F.) and drawing vacuum on the collagen; wherein a vacuum pressure is at least 100 mTorr.

An insoluble collagen product, as defined herein can provide a more stable and durable scaffold for cell growth and tissue regeneration, due to its highly crosslinked structure. This can be important in load-bearing applications, such as bone or cartilage tissue engineering, where the scaffold needs to withstand mechanical forces. Insoluble collagen can also have improved resistance to enzymatic degradation.

Insoluble collagen will be homogenized in water and may be non-dialyzed collagen, or may be dialyzed to change molecular weight, remove impurities and/or adjust the pH. Homogenizing may be accomplished by blending, shearing or cutting the lipid removed tissue.

An insoluble collagen may further be lyophilized, including freezing the collagen and then heating the frozen collagen to a lyophilization temperature of at least 50° C. (70° F.) and drawing vacuum on the collagen; wherein a vacuum pressure is at least 100 mTorr.

The distinct collagen components soluble and insoluble may be collected and further dried and lyophilized. As described herein the two distinct products may be mixed in a ratio to form a mixed composite collagen product. The ratio may be a weight ratio of the soluble collagen component to the insoluble collagen component. This composite collagen product may have an engineered ratio of soluble and insoluble collagen designed for specific application. The ratio of the soluble and insoluble collagen components in the composite, affects the chemical, mechanical and biological properties. The properties that can be tailored by a change in the ratio of the components include, but are not limited to, durometer, or hardness, stiffness, modulus, elongation at break, max load, water absorption, rate of absorption or break down as measured by the rate of weight loss. The ratio of the components can increase or decrease how long it takes for the product to break down. A first ratio of soluble to insoluble components may have a time to reach half an initial max load that is double the time to reach half an initial max load of a second ratio of soluble to insoluble components, as an example.

This invention includes a method of controlling the concentration of soluble and insoluble collagen or ratio in a composite collagen product. This method may include separating the components as described herein and then mixing them together in an engineered ratio to provide the chemical, mechanical and biological properties desired.

A composite collagen product may be made into a sheet or rod, or tube or other shape for a particular purpose. The ratio of the soluble to insoluble collagen components may be varied through the thickness of the composite collagen product, wherein a first layer or an outer layer has a ratio of soluble collagen to insoluble collagen that is at least about 25% different from a ratio of soluble collagen to insoluble collagen on a second layer, such as an inner layer, opposite the outer layer, for example. The difference in soluble collagen to insoluble collagen from a first layer to a second layer may be 50% different or more, about 100% different or more, about 200% different or more, about 500% different or more and any range between and including the percentages provided. As an example, a collagen patch may be configured with a low ratio of soluble to insoluble collagen on the outer layer to slow degradation from the exposed surface but may have a high ratio of soluble to insoluble collagen on an inside layer to enable fixation to a biological surface for example, such as tissue or an organ and the percentage difference in the ratios may be about 100% or more.

Prior to separating, the extract collagen may be removed from solution as an integral composite collagen product which may be further dried and lyophilized are required for the application.

A soluble collagen product, as defined herein, will dissolve in 1 mM of acetic to 1000 mM, having a pH of between about 0.5 pH to 4.0 pH within about one week.

An insoluble collagen, as defined herein, will not dissolve in 1 mM of acetic to 1000 mM, having a pH of between about 0.5 pH to 4.0 pH within a week and will maintain a shape such as a sheet of material after one week.

A minced dermis tissue, as used herein, is dermis tissue that is cut into pieces, such as having dimensions of about 25 mm or less, about 15 mm or less, or about 10 mm or less, about 5 mm or less, and any range between and including the values provided.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
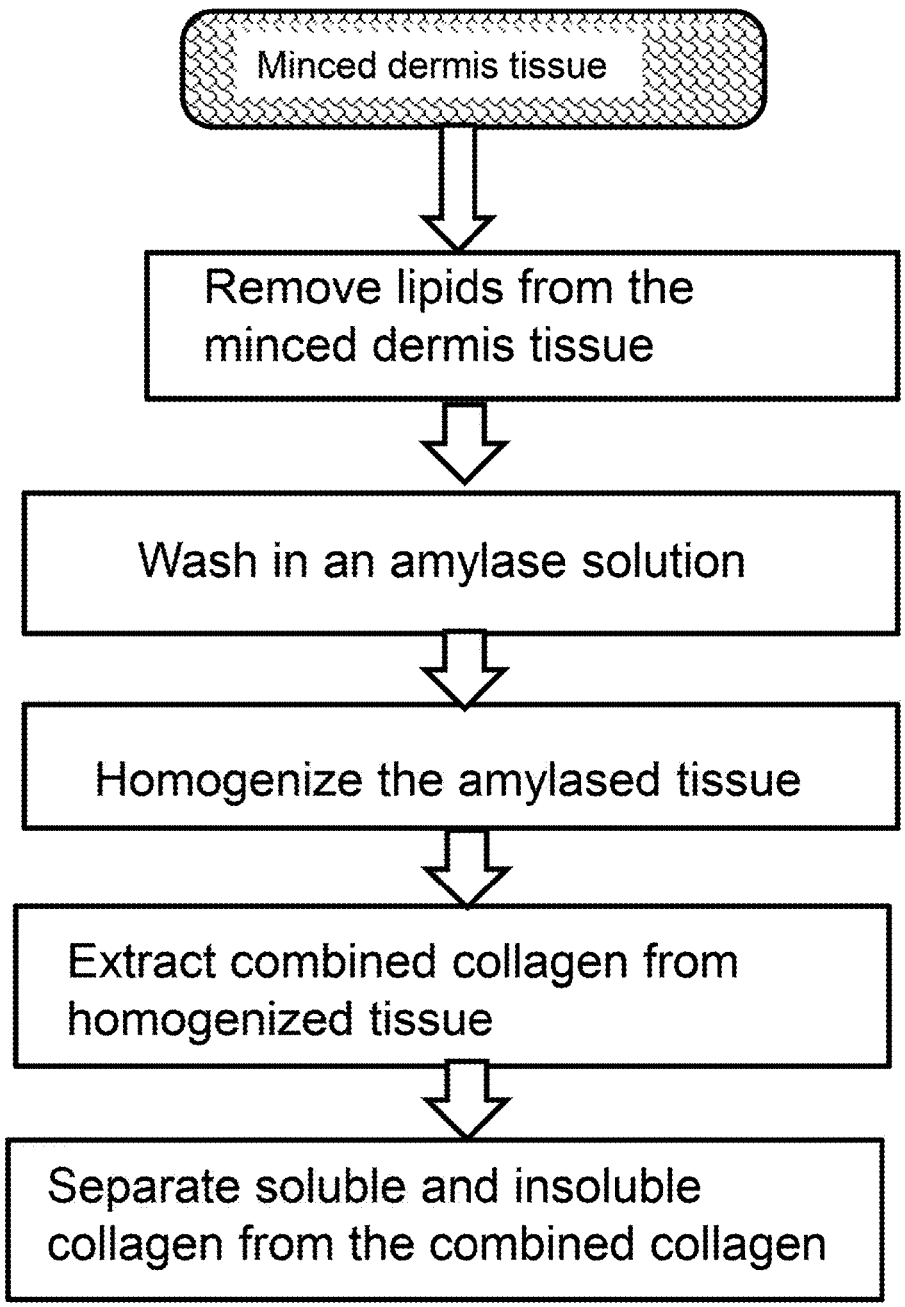
FIG. 1 shows a flow diagram of an exemplary process for the production of a soluble collagen product and an insoluble collagen product from mammalian dermis tissue.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be an included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, the process for the production of a soluble collagen product and an insoluble collagen product from mammalian dermis tissue includes washing in an amylase solution and the homogenizing the tissue under cold conditions. The collagen is then extracted from the homogenized tissue and subsequently separated such as by centrifugation.

Figure 2:
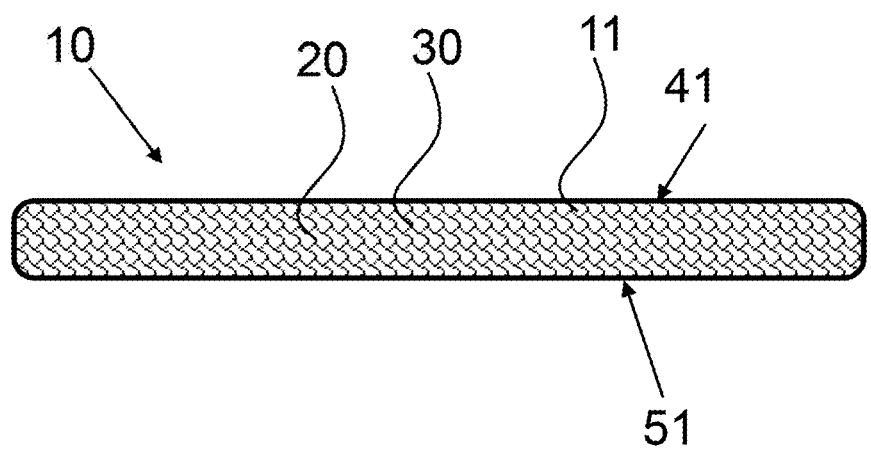
FIG. 2 shows a composite collagen product having a ratio of soluble collagen to insoluble collagen.

As shown in FIG. 2, composite collagen product 10 is composed of a single layer. The composition of the layer of the collagen product can be controlled by changing the concentration of soluble collagen 20 to insoluble collagen 30. A composite collagen product 10 can be composed of double or multiple layers and can be tailored by changing the ratio of soluble to insoluble collagen. The composite collagen 11 has a first surface 41 and an opposing second surface 51. This is a sheet of composite collagen.

Figure 3:
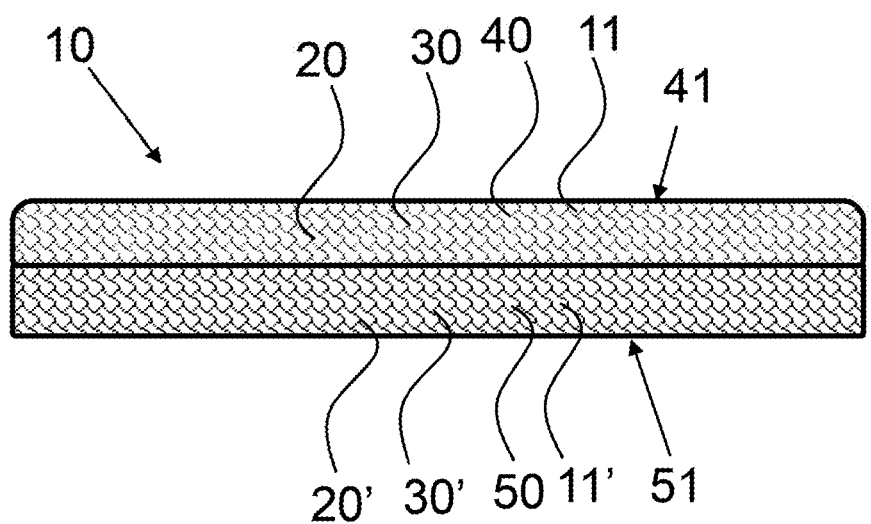
FIG. 3 shows a composite collagen product having a ratio of soluble collagen to insoluble collagen and multiple layers of composite collagen.

As shown in FIG. 3, a composite collagen product 10 has a ratio of soluble collagen 20 to insoluble collagen 30 that may be tailored for a given application. As shown, the composite collagen product has a first layer 40 of composite collagen 11 having a first ratio of soluble collagen 20 to insoluble collagen 30 and a second layer 50 of composite collagen 11' having a second ratio of soluble collagen 20' to insoluble collagen 30'. The first layer 40 of composite collagen 11 extends to or is on the first surface 41 and the second layer 50 of composite collagen 11' extends to or is on the second surface 51. Note that one or more additional layers of composite collagen may be configured between the first layer 40 and second layer 50.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A process for the production of a soluble collagen product and an insoluble collagen product from mammalian dermis tissue comprising:
    a) providing minced dermis tissue from said mammalian dermis tissue:
    b) removing lipids from the minced dermis tissue comprising:
        i) providing a first lipid removal solution comprising:
            chloroform;
            methanol; and
            hexane;
        ii) washing the minced dermis tissue with said first lipid removal solution for a washing time of at least 8 hours;

c) providing an enzymatic solution comprising:
   i) water; and
   ii) amylase;
d) after washing in said first lipid removal solution, washing the minced dermis tissue in the enzymatic solution to produce an enzymatic solution washed tissue;
e) homogenizing the enzymatic solution washed tissue at temperature of no more than 40° C. to produce homogenized tissue;
f) providing extraction solution;
g) extracting both said soluble collagen and said insoluble collagen from the homogenized tissue by washing the homogenized tissue in said extraction solution to produce an extracted collagen; and
h) separating said soluble collagen and said insoluble collagen from said extracted collagen.

2. The process of claim 1, wherein the minced mammalian dermis tissue has a length and width of no more than 10 mm.

3. The process of claim 1, wherein the first lipid removal solution further comprises a buffer.

4. The process of claim 1, wherein the first lipid removal solution further comprises an antifoaming agent that is tributyl phosphate.

5. The process of claim 1, further comprising washing the minced dermis tissue in a second lipid removal solution comprising an organic solvent.

6. The process of claim 5, wherein the organic solvent of the second lipid removal solution comprises ethanol.

7. The process of claim 5, wherein the organic solvent of the second lipid removal solution is selected from the group of methanol, chloroform and a mixture of methanol and chloroform.

8. The process of claim 1, wherein the amylase has a concentration of at least 0.1 mg/ml in the amylase solution.

9. The process of claim 1, wherein the amylase solution comprises a buffer.

10. The process of claim 9, wherein the buffer of the amylase solution comprises a phosphate buffer.

11. The process of claim 1, wherein the temperature of homogenizing is maintained above 0° C. and below 10° C.

12. The process of claim 1, wherein the extraction solution comprises acetic acid.

13. The process of claim 12, wherein the extraction solution comprises pepsin.

14. The process of claim 1, wherein separating said soluble collagen and said insoluble collagen comprises centrifuging the extracted collagen.

* * * * *